United States Patent
Morejon

(10) Patent No.: US 11,395,897 B1
(45) Date of Patent: *Jul. 26, 2022

(54) CONNECTOR ASSEMBLY FOR A MEDICAL VENTILATOR SYSTEM

(71) Applicant: Orlando Morejon, Miami, FL (US)

(72) Inventor: Orlando Morejon, Miami, FL (US)

( * ) Notice: Subject to any disclaimer, the term of this patent is extended or adjusted under 35 U.S.C. 154(b) by 389 days.

This patent is subject to a terminal disclaimer.

(21) Appl. No.: 16/405,678

(22) Filed: May 7, 2019

Related U.S. Application Data

(63) Continuation-in-part of application No. 14/753,445, filed on Jun. 29, 2015, now Pat. No. 10,279,137.

(Continued)

(51) Int. Cl.
  *A61M 16/08* (2006.01)
  *A61M 16/00* (2006.01)
  (Continued)

(52) U.S. Cl.
  CPC .... *A61M 16/0816* (2013.01); *A61M 16/0463* (2013.01); *A61M 16/201* (2014.02)

(58) Field of Classification Search
  CPC .. A61M 16/0463; A61M 16/04; A61M 16/20; A61M 16/0816; A61M 16/0833;
  (Continued)

(56) References Cited

U.S. PATENT DOCUMENTS 1,567,500 A  12/1925 Hein
2,910,981 A  11/1959 Wilson et al.
(Continued)

FOREIGN PATENT DOCUMENTS

CN  1284845 A  2/2001
CN  1191794    3/2005
(Continued)

OTHER PUBLICATIONS

Intensive Care Society National Guidelines—When and how to wean, Intensive Care Society, Jan. 2007 (Year: 2007).
(Continued)

*Primary Examiner* — Margaret M Luarca
(74) *Attorney, Agent, or Firm* — Malloy & Malloy, P.L.

(57) ABSTRACT

A connector assembly for a medical ventilator including a housing having a plurality of ports including an intervention port disposed and structured to introduce an intervention device into said housing and a patient airway. The plurality of ports also include a ventilator port and an airway port respectively disposed and structured to connect a ventilator and an artificial airway in fluid communication with one another. A valve structure is movably and removably disposed within a valve port and is disposable between open and closed positions. The closed position comprising the intervention port sealed from fluid communication with the housing and a closed ventilator circuit defining fluid communication between the ventilator port and the airway port. The open orientation comprising the intervention port disposed in communicating relation with the airway port concurrent to fluid communication between the ventilator port and the airway port.

13 Claims, 7 Drawing Sheets

Related U.S. Application Data

(60) Provisional application No. 62/017,991, filed on Jun. 27, 2014.

(51) Int. Cl.
*A61M 16/20* (2006.01)
*A61M 16/04* (2006.01)

(58) Field of Classification Search
CPC .............. A61M 39/1055; A61M 39/10; A61M 39/223; A61M 1/0023; A61M 1/035; F16K 6/0492
See application file for complete search history.

(56) References Cited

U.S. PATENT DOCUMENTS

| | | |
|---|---|---|
| 3,064,294 A | 11/1962 | Stocking |
| 3,173,418 A | 3/1965 | Baran |
| 3,398,417 A | 8/1968 | Erwin |
| 3,508,554 A | 4/1970 | Sheridan |
| 3,610,247 A | 10/1971 | Jackson |
| 3,638,655 A | 2/1972 | Doherty |
| 3,769,983 A | 11/1973 | Merav |
| 3,810,474 A | 5/1974 | Cross |
| 3,965,975 A | 6/1976 | Edmundson |
| 3,991,762 A | 11/1976 | Radford |
| 3,995,643 A | 12/1976 | Merav |
| 4,018,231 A | 4/1977 | Wallace |
| 4,021,265 A | 5/1977 | Guenther |
| 4,026,311 A | 5/1977 | Jackson |
| 4,088,131 A | 5/1978 | Elam |
| 4,327,723 A | 5/1982 | Frankhouser |
| 4,417,576 A | 11/1983 | Baran |
| 4,423,725 A | 1/1984 | Baran et al. |
| 4,489,741 A | 12/1984 | Ogasawara |
| 4,515,592 A | 5/1985 | Frankhouser |
| 4,569,344 A | 2/1986 | Palmer |
| 4,637,814 A | 1/1987 | Leiboff |
| 4,638,539 A | 1/1987 | Palmer |
| 4,649,913 A | 3/1987 | Watson |
| 4,693,243 A | 9/1987 | Buras |
| 4,696,296 A | 9/1987 | Palmer |
| 4,723,549 A | 2/1988 | Wholey et al. |
| 4,762,125 A | 8/1988 | Leiman et al. |
| 4,787,659 A | 11/1988 | Durham |
| 4,825,859 A | 5/1989 | Lambert |
| 4,836,199 A | 6/1989 | Palmer |
| 4,872,579 A | 10/1989 | Palmer |
| 4,938,741 A | 7/1990 | Lambert |
| 4,892,095 A | 9/1990 | Nakhgevany |
| 4,981,470 A | 1/1991 | Bombeck, IV |
| 5,002,557 A | 3/1991 | Hasson |
| 5,003,657 A | 4/1991 | Bolteau et al. |
| 5,030,213 A | 7/1991 | Rumberger et al. |
| 5,048,518 A | 9/1991 | Eliachar et al. |
| 5,049,131 A | 9/1991 | Deuss |
| 5,057,093 A | 10/1991 | Clegg et al. |
| 5,119,811 A | 6/1992 | Inglis et al. |
| 5,127,398 A | 7/1992 | Stone |
| 5,143,062 A | 9/1992 | Peckham |
| 5,146,916 A | 9/1992 | Catalani |
| 5,176,638 A | 1/1993 | Don Michael |
| 5,176,697 A | 1/1993 | Hasson et al. |
| 5,214,474 A | 5/1993 | Ishizuka |
| 5,259,371 A | 11/1993 | Tonrey |
| 5,259,377 A | 11/1993 | Schroeder |
| 5,269,759 A | 12/1993 | Hernandez et al. |
| 5,285,777 A | 2/1994 | Beckwith |
| 5,314,417 A | 5/1994 | Stephens et al. |
| 5,353,787 A | 10/1994 | Price |
| 5,386,741 A | 2/1995 | Rennex |
| 5,423,760 A | 6/1995 | Yoon |
| 5,437,645 A | 8/1995 | Urban et al. |
| 5,447,497 A | 9/1995 | Sogard et al. |
| 5,499,625 A | 3/1996 | Frass et al. |
| 5,522,831 A | 6/1996 | Sleister et al. |
| 5,538,509 A | 7/1996 | Dunlap et al. |
| 5,542,938 A | 8/1996 | Avellanet et al. |
| 5,620,456 A | 4/1997 | Sauer et al. |
| 5,642,726 A | 7/1997 | Owens et al. |
| D385,627 S | 10/1997 | Cook et al. |
| 5,674,209 A | 10/1997 | Yarger |
| 5,687,714 A | 11/1997 | Kolobow et al. |
| 5,709,691 A | 1/1998 | Morejon |
| 5,711,294 A | 1/1998 | Kee et al. |
| 5,713,869 A | 2/1998 | Morejon |
| 5,720,282 A | 2/1998 | Wright |
| 5,746,199 A * | 5/1998 | Bayron .............. A61M 16/0463 128/205.24 |
| 5,752,509 A | 5/1998 | Lachmann et al. |
| 5,775,328 A | 7/1998 | Lowe et al. |
| 5,843,115 A | 12/1998 | Morejon |
| 5,865,178 A | 2/1999 | Yock |
| 5,931,163 A | 8/1999 | Stegmann et al. |
| 6,082,361 A | 7/2000 | Morejon |
| 6,273,088 B1 | 8/2001 | Hillsman |
| D449,379 S | 10/2001 | Fuhr |
| 6,318,368 B1 | 11/2001 | Morejon |
| 6,468,279 B1 | 10/2002 | Reo |
| 6,494,208 B1 | 12/2002 | Morejon |
| 6,679,262 B1 | 1/2004 | Morejon |
| D492,032 S | 6/2004 | Muller et al. |
| D492,775 S | 7/2004 | Doelling et al. |
| 6,763,831 B2 | 7/2004 | Sniadack |
| 6,919,057 B2 | 7/2005 | Halstead et al. |
| 7,060,135 B2 | 6/2006 | Morejon |
| D569,515 S | 5/2008 | DeLonzor et al. |
| 7,513,901 B2 | 4/2009 | Scifert et al. |
| 7,588,033 B2 | 9/2009 | Wondka |
| 7,669,600 B2 | 3/2010 | Morejon |
| D615,197 S | 5/2010 | Koh et al. |
| D634,424 S | 3/2011 | Morejon |
| D699,348 S | 2/2014 | Morejon |
| 8,695,593 B2 | 4/2014 | Tehrani |
| 10,279,137 B1 | 5/2019 | Morejon |
| 2001/0004893 A1 | 6/2001 | Biondi et al. |
| 2002/0069877 A1 | 6/2002 | Villareal et al. |
| 2002/0165538 A1 | 11/2002 | Schneiter |
| 2003/0111078 A1 | 6/2003 | Habashi |
| 2003/0209246 A1 | 11/2003 | Schroeder et al. |
| 2004/0003814 A1 | 1/2004 | Banner et al. |
| 2004/0084050 A1 | 5/2004 | Baran |
| 2004/0123866 A1 | 7/2004 | Berthon-Jones |
| 2005/0039754 A1 | 2/2005 | Simon |
| 2005/0172971 A1 | 8/2005 | Kolobow et al. |
| 2006/0130847 A1 | 6/2006 | Morejon |
| 2006/0263283 A1 | 11/2006 | Egan et al. |
| 2008/0066782 A1 | 3/2008 | Langford |
| 2008/0295839 A1 | 12/2008 | Habashi |
| 2010/0012122 A1 | 1/2010 | Shaffer et al. |
| 2010/0186748 A1 | 7/2010 | Morejon |
| 2010/0199448 A1 | 8/2010 | Vazales et al. |
| 2011/0023888 A1 | 2/2011 | Vazales et al. |
| 2011/0155135 A1 | 6/2011 | Chiu |
| 2011/0313689 A1 | 12/2011 | Holley |
| 2012/0006364 A1 | 1/2012 | Kim |
| 2012/0137250 A1 | 5/2012 | Milne |
| 2013/0133644 A1 | 5/2013 | Rosekrans et al. |
| 2013/0312755 A1 | 11/2013 | Ho |
| 2014/0150782 A1 | 6/2014 | Vazales et al. |
| 2014/0165309 A1 | 6/2014 | Frey et al. |
| 2014/0190523 A1 | 7/2014 | Garvey |
| 2015/0276772 A1 | 10/2015 | Dockrill et al. |
| 2015/0343182 A1 | 12/2015 | Vazales |
| 2018/0250096 A1 | 9/2018 | Morejon |

FOREIGN PATENT DOCUMENTS

| | | |
|---|---|---|
| CN | 102971090 | 7/2015 |
| EP | 0330376 A2 | 8/1989 |
| EP | 1056412 A1 | 12/2000 |
| EP | 1629765 | 3/2006 |
| EP | 2714175 | 4/2014 |
| EP | 2990060 | 3/2016 |

(56) References Cited

FOREIGN PATENT DOCUMENTS

| FR | 2803755 | 7/2001 |
|----|---------|--------|
| WO | WO9403226 A1 | 2/1994 |
| WO | WO9935998 | 7/1999 |
| WO | WO2007081264 | 7/2007 |
| WO | WO2010091309 | 8/2010 |
| WO | WO11094390 | 8/2011 |
| WO | WO11094517 | 8/2011 |
| WO | WO11103403 | 8/2011 |

OTHER PUBLICATIONS

The five P's spell positive outcomes for ARDS patients, American Nurse Today, Mar. 2007, vol. 2, No. 3 (Year: 2007).
Lermitte, et al "Weaning from Mechanical Ventilation", Continuing Education in Anesthesia, vol. 5, No. 4, 2005 (Year: 2005).

\* cited by examiner

CONNECTOR ASSEMBLY FOR A MEDICAL VENTILATOR SYSTEM

CLAIM OF PRIORITY

The present application is a continuation-in-part application of U.S. patent application Ser. No. 14/753,445, filed on Jun. 29, 2015, which is set to mature into U.S. Pat. No. 10,279,137 on May 7, 2019, which a claim of priority is made under 35 U.S.C. Section 119(e) to a provisional patent application that is currently in the U.S. Patent and Trademark Office, namely, that having Ser. No. 62/017,991 and a filing date of Jun. 27, 2014, and which is incorporated herein by reference.

BACKGROUND OF THE INVENTION

Field of the Invention

This invention is directed to a connector assembly for a medical ventilator which facilitates the use of a variety of interventional airway devices in conjunction with a closed ventilator circuit establishing fluid communication between a ventilator and a patient's original or natural airway. Accordingly, the introduction, interventional use, withdrawal, removal, and/or transition of different interventional devices can be accomplished without the loss of airway pressure in the ventilator circuit.

Description of the Related Art

Many patients in a hospital, including patients in an Intensive Care Unit ("ICU"), must be fitted with an artificial airway, such as an endotracheal tube, to facilitate their respiration. Typically, the artificial airway tube comprises an elongate, semi-rigid lumen which is inserted into a patient's nose or throat and projects down into airflow communication with the patient's respiratory system. As such, the patient either directly, or with the aid of a respiratory unit, is able to breathe more effectively through the artificial airway tube. Also, a manifold or connector structure is used to connect the artificial airway or endotracheal tube to a source of breathable gas.

Recent studies have determined, however, that the accumulation of dried tracheo-bronchial secretions on the interior wall surface of an operating artificial airway tube effectively decreases the lumen cross section, and thereby significantly increases the work of breathing for the intubated patient. Moreover, increasing the work of breathing for the patient necessitates that a higher level of support be provided to compensate, and often results in the patient's intubation period and ICU stay being significantly prolonged. Furthermore, it is also seen that thick secretions on the walls of the artificial airway tube often serve as a nidus for continued infection in the lungs, leading to added morbidity and hospital costs for the incubated patient.

Therefore, while a patient is attached to the respiratory support system, it is periodically necessary to aspirate fluids and/or secretions from the patient's trachea and lungs. In the performance of prior art techniques it was frequently necessary to disassemble part of the respiratory support system by removing the ventilator manifold/connector and inserting an intervention device such as, but not limited to, a suction catheter into the artificial airway. Fluid and like contaminants were then suctioned from the patient. Thereafter, the suction catheter was removed and the respiratory support system, including the manifold/connector, was reassembled. However, due to the interruption of respiratory support during such an interventional procedure, a patient's blood oxygen can often drop and carbon monoxide can reach an unacceptable level. Additionally, unless a sufficient positive end expiratory pressure (PEEP) level is maintained there is a possibility that the lungs of the patient will collapse. Moreover, procedures of this type may have to be performed numerous times per day and during relatively long periods of hospitalization of the patient.

In order to overcome well recognized problems of the type set forth above it is important to provide respiratory equipment that will minimize patient discomfort. In addition, improvement in the equipment and/or operative components of a respiratory and or ventilation system should have sufficient operative versatility to treat patients of different age groups. In recognizing such procedural problems including the maintaining adequate pressure in a ventilation system, numerous attempts have been made to provide improved facilities which serve to maintain a continuous flow of oxygen from the respirator device through aforementioned manifold/connector and the artificial airway tube to the lungs of the patient. Such known attempts intended to be operative to facilitate the insertion and retraction of various types of intervention devices such as, but not limited to, the aforementioned suction catheter. However, known attempts of this type failed to provide an operable system capable of performing machine assisted respiration without disconnecting the respirator a disassembly of the interposed manifold/connector.

Accordingly, there is a need in the medical profession for a connector assembly structured for use with a medical ventilator system, wherein a completely closed ventilator circuit is established and maintained from the start of mechanical ventilation until the patient is ready for removal from ventilator support and/or removal of the artificial airway. Moreover, an improved and proposed connector assembly should be structured to include a plurality of ports including, but not limited to, an intervention port. As such, the introduction of any one or more of a variety of different intervention devices will be facilitated in a manner which avoids the loss of airway pressure (PEEP) during all types of interventional procedures involving the airway and transitional steps associated therewith. Moreover, the structural and operative features of such a proposed connector assembly and associated ventilation components eliminates interruptions in the patient's ventilator support and oxygenation while preserving adequate pressure during all interventional procedures.

SUMMARY OF THE INVENTION

The present invention is directed to a connector assembly for a medical ventilator system which facilitates the use of any one of a plurality of different interventional airway devices, for introduction into the natural or artificial airway of a ventilated patient, without loss of airway pressure in a closed ventilator circuit.

More specifically, the connector assembly includes a housing having an at least partially hollow interior and a plurality of ports disposed in communicating relation with the hollow interior and one another. Further, the plurality of ports comprise a ventilator port and an airway port respectively disposed and structured to connect the ventilator source and an artificial airway to the housing in fluid communication with one another. The plurality of ports also include an intervention port disposed and structured to introduce any one of a plurality of different type intervention devices into the housing. When applied, the intended intervention device extends through the intervention port, into the interior of the housing and there through into the airway port. The intervention device, depended on its intended use, may pass into and along the natural patient airway or an inserted artificial airway tubing or like structure.

A valve structure is movably and preferably removably connected to the housing by insertion into a valve port. When operatively disposed within the valve port, the valve structure is disposable between an open position and a closed position relative to the intervention port. As such, the closed position of the valve structure comprises the intervention port being sealed from physical or fluid communication with the hollow interior of the housing. In addition a closed ventilator circuit is established within the housing so as to define bidirectional fluid communication between the ventilator port and the airway port, as well as any ventilator and/or airway tubing connected to the housing. In contrast, the open position of the valve structure comprises the intervention port being opened into communicating relation with the airway port. Concurrently, while the intervention port is open, bidirectional fluid communication is maintained between the ventilator port and the airway port.

Additional structural and operational features of the plurality of ports of the housing include the airway port, ventilator port an intervention port all preferably including a round or circular cross-sectional configuration. Further the airway port may include a standard 15 mm interior diameter dimensioned to fit industry-standard 15 mm outside diameter artificial airway tube or tracheostomy tube connectors. In the alternative, the airway port could be configured to replace the artificial airway tube conical connector and be formed of varying outside diameter sizes to fit the inside diameter of artificial airway tubes, with an internal diameter matching that of the artificial airway tube conical connectors.

As indicated the ventilator port is structured for connection to ventilator tubing associated with the ventilator system. The ventilator port will preferably, but not necessarily, be perpendicular to the axis of the airway port. However the disposition of the ventilator port may be offset between 90 and 180 degrees. between the airway port and the intervention port. The ventilator port can be configured with a standard 22 mm outside diameter to accept respiratory circuit tubing of 22 mm inside diameter. In the alternative, the ventilator port can be configured with a 15 mm outside diameter to accept standard respiratory circuit tubing connectors with a 15 mm inside diameter. Yet an additional alternative can include the ventilator port being configured with an inside diameter of greater than 15 mm and an outside diameter of generally about 22 mm.

As also indicated, the intervention port is structured for access, by an intervention device, to the artificial airway tubing such as the aforementioned endotracheal tube or tracheotomy tube, connected to the airway port, as well as a natural airway of the patient. The intervention device, depended upon its intended use may be applied for interventional airway procedures or other diagnostic or therapeutic procedures such as, but not limited to suctioning, clearance of secretions or biofilms, blood, etc. Also, bronchoscopy and bronchoscopically guided procedures including, but not limited to, biopsies or retrieval of foreign bodies and/or deployment of stents or other implantable medical devices can be accomplished. As such, the intervention port would preferably be axially aligned with the airway port, such as being disposed at a 180.degree. angle from the airway port. In the alternative, the intervention port may be offset generally between 90.degree. and 180.degree. from the airway port. Further, the intervention port can be configured to any appropriate size or shape but would preferably include the aforementioned round cross-sectional configuration. When so configured, it may have an outer diameter from 1 mm to generally about 23 mm. However in one preferred embodiment the intervention port as an outer diameter of generally about or less than 15 mm.

It is also to be noted that the intervention port may include an external feature operatively structured to reversibly interlock with a matching feature on an inner lumen of the interventional device applied to the housing of the connector assembly.

The of aforementioned valve port may be appropriately dimensioned and configured to receive the valve structure therein in a manner which facilitates its rotational or other preferred movement between the open and closed positions. Accordingly, one preferred embodiment includes the valve structure having a valve body removably disposed within the valve port and rotationally disposable therein between the open and closed positions. As indicated, the valve structure and/or valve body is removably disposed within the interior of the valve port. However, with the valve body removed from the valve port and the housing, the valve port remains in full communication with the interior of the housing in fluid communication with the airway port and any airway tubing or like structure connected thereto. Accordingly, the valve port may serve as an additional functional port for bidirectional, constant an unobstructed fluid flow with the airway port. Therefore, the valve port may include a standard 22 mm outside diameter to connect respiratory circuit tubing of 22 mm inside diameter. In the alternative, the valve port can be configured with a 15 mm outside diameter to accept standard respiratory circuit tubing connector with a 15 mm inside diameter. Yet another alternative includes the valve port being configured with an inside diameter of greater than 15 mm but an outside diameter of generally about 22 mm.

Yet additional features of the valve port may include a specific structural or operative configuring such as by an added "step" structure or member. As such the step structure may be configured to interact with the valve body so as to establish a preferred, correct operative orientation and prevent introduction of the valve body in an incorrect orientation. As a result, unintended obstruction of the bidirectional fluid flow within the ventilator circuit between the ventilator port and the airway port will be prevented.

Yet another structural and operative feature of one or more preferred embodiments of the present invention may include a gasket structure or assembly comprising at least one gasket or a set of gaskets structured to establish a sealing engagement with interventional devices entering the intervention port. Further, the one or more gaskets may be disposed and structured to seal the intervention port independently or in combination with and during use of an intended interventional device of a specific diameter. The inclusion of the one or more gaskets, in the manner described, provides a continuous preservation of airway pressure (PEEP) despite the fact that the "closed ventilator circuit" is being accessed by a variety of interventional devices intended to perform different clinical procedures on the patient.

As also indicated, the valve structure preferably includes a valve body rotationally or otherwise disposable within the valve port as it moves between the open and closed positions, relative to the intervention port. Also, the valve structure includes a retaining assembly including one or more retaining members connected to and/or mounted on the valve body of the valve structure. The one or more retaining members are disposable into movable, retaining engagement with exterior portions of the housing. Accordingly, rotation or other preferred movement of the valve body within the valve port may occur concurrently to the one or more retaining members being disposed in movable, interconnecting, retaining engagement with the exterior of the housing.

The valve body may also include an end portion which is accessible exteriorly of the connector housing and which may include a handle or gripping structure. The gripping structure facilitates the manual rotational or other movement of the valve body between the open and closed positions. Accordingly, the valve body may be selectively disposed such that a valve stem, or other appropriate portion of the valve body, partially or completely occludes the intervention port, while preserving fluid flow or communication through and between the ventilator port and the airway port. As such, when in the closed orientation the valve body or valve stem prevents communication or access between the intervention port and the hollow interior of the connector housing, including access to the airway port. In contrast, a fully open orientation the valve body allows unimpeded bidirectional fluid flow past the valve mechanism and between the ventilator port and the airway port. Further, the cross-sectional lumen area at the level of the valve mechanism approximates and is self-maintained to the same degree as the cross-sectional lumen area of the airway connection port lumen. This feature allows unrestricted and near frictionless access to the patient airway during both insertion and withdrawal of intervention devices. In all of its orientations, the valve structure ensures full and uninterrupted bidirectional fluid flow between the ventilator port and the airway port as well as between the ventilator tubing and the airway tubing respectively connected thereto.

As indicated, rotation or other movement of the valve structure between the open and closed positions occurs while the body of the valve, or at least a major portion thereof is disposed within the valve port. Selected manual rotational or other movement of the valve structure and an accurate positioning of the valves body or valve stem may be further facilitated by the provision of a plurality of detents or other structures which provide a tactile feedback to the operator as to the actual orientation of the valve body into or between the open and closed positions.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
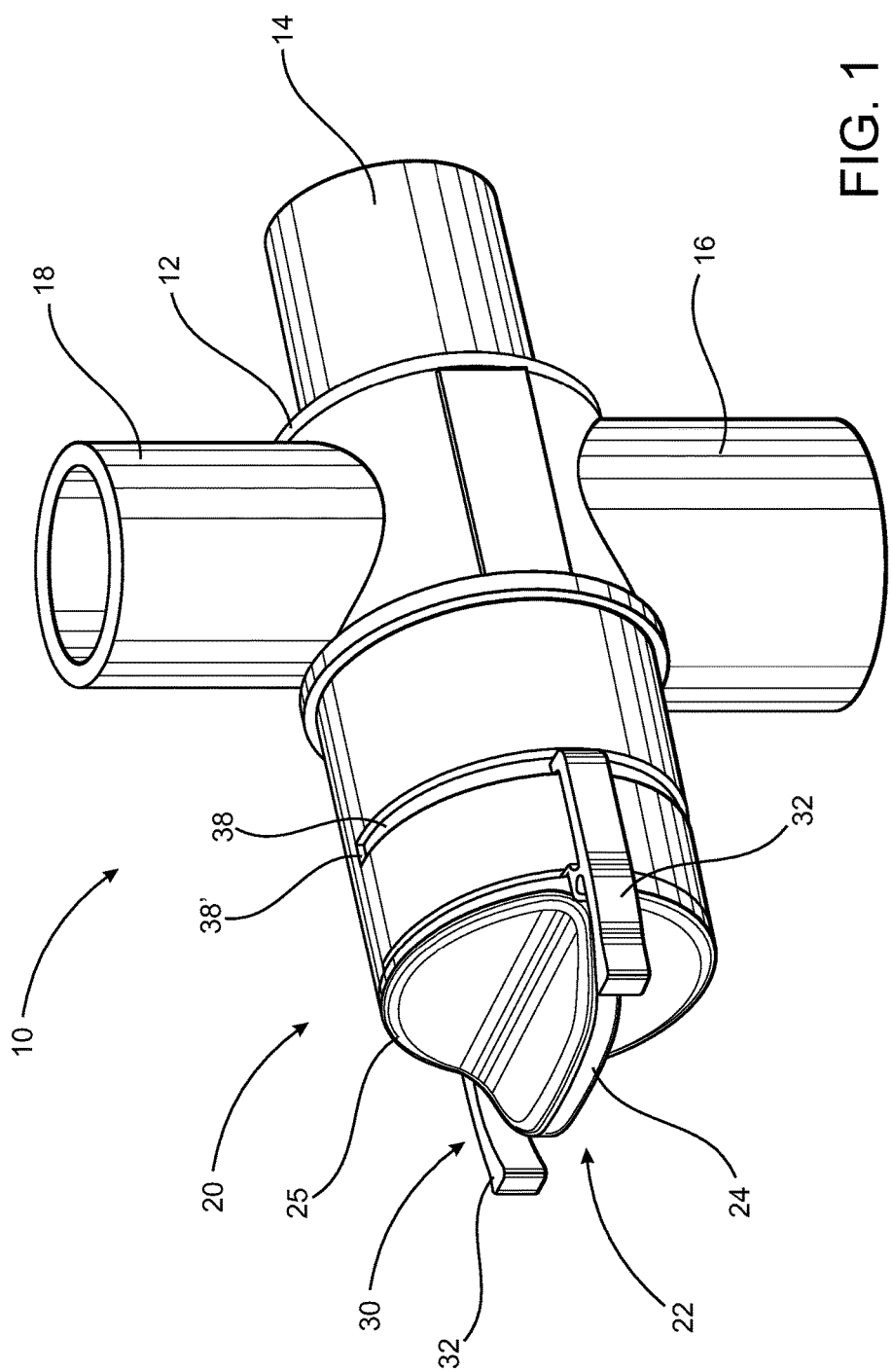
FIG. 1 is a perspective view of one preferred embodiment of the assembled connector assembly of the present invention, in an open position.

As represented in the accompanying Figures, the present invention is directed to a connector assembly generally indicated as 10 structured for use in establishing a closed ventilator circuit for a medical ventilator system. Further, the structural and operative features of the connector assembly 10 are such as to facilitate the use of any one a plurality of different intervention devices of the type used on ventilator patients. Further, such intervention devices may be used without compromising the pressure and/or intended bidirectional fluid flow between the ventilator source and the natural or artificial patient airway.

More specifically, the connector assembly 10 includes a connector housing 12 having an at least partially hollow interior and a plurality of ports. Further, the plurality of ports at least include a ventilator port, generally indicated as 14, and an airway port, generally indicated as 16. In addition, an intervention port is generally indicated as 18. As set forth in detail herein the dimensions and configurations of each of the plurality of ports 14, 16, 18, etc. may have a substantially round sectional configuration and be dimensioned for connection and/or attachment to ventilator tubing, airway tubing, intervention devices, etc. In more specific terms, the ventilator port 14 may include a male configuration with an appropriately dimensioned outside diameter to facilitate attachment to a ventilator tubing which in turn leads to the ventilator source. The airway port 16 may have a female structural configuration to facilitate attachment to an artificial airway tubing applied to the patient's natural airway. The intervention port 18 may be appropriately dimensioned and configured to accommodate any one of a plurality of different types and different sizes of intervention devices used in ventilation therapy and procedures. Further, the ventilator port 14, airway port 16 and intervention port 18 are disposed at a substantially 90.degree. spacing from one another. As such, the intervention port 18 is disposed in substantially axially aligned relation to the airway port 16 to further facilitate passage of an interventional device through the intervention port 18 and through the hollow interior of the connector housing 12 into and through the airway port 16 for continued passage into the natural or artificial airway associated with the ventilated patient. However, different relative locations of the ventilation port 14, airway port 16 and intervention port 18 may be utilized. Also additional ports other than those ports set forth throughout the Figures may be added to further facilitate the variable and effective use of the connector assembly 10 as defined in the one or more preferred embodiments of the present invention.

As also represented throughout the Figures, the connector assembly 10, including the housing 12 may also include a valve port generally indicated as 20. The valve port 20 is dimensioned and configured to movably and removably receive a valve structure, generally indicated as 22, represented in greater detail in FIG. 6. The cooperative dimensioning between the interior of the valve port 20 relative to the exterior dimensioning of the valve body 26 of the valve structure 22 is such as to facilitate a predetermined movement of the valve body 26 within the interior of the valve port 20. In the embodiment represented, the valve structure 22 is rotationally disposed within the interior of the valve port 20 so as to be selectively disposed between an open position and a closed position. Further, such selective movement of the valve body 26 is preferably accomplished by the inclusion of a handle or gripping member 24 disposed on an end portion or 25 which extends, at least partially, out of the valve port 20 so as to be exteriorly accessible when operatively disposed on or connected to the housing 12.

Figure 2:
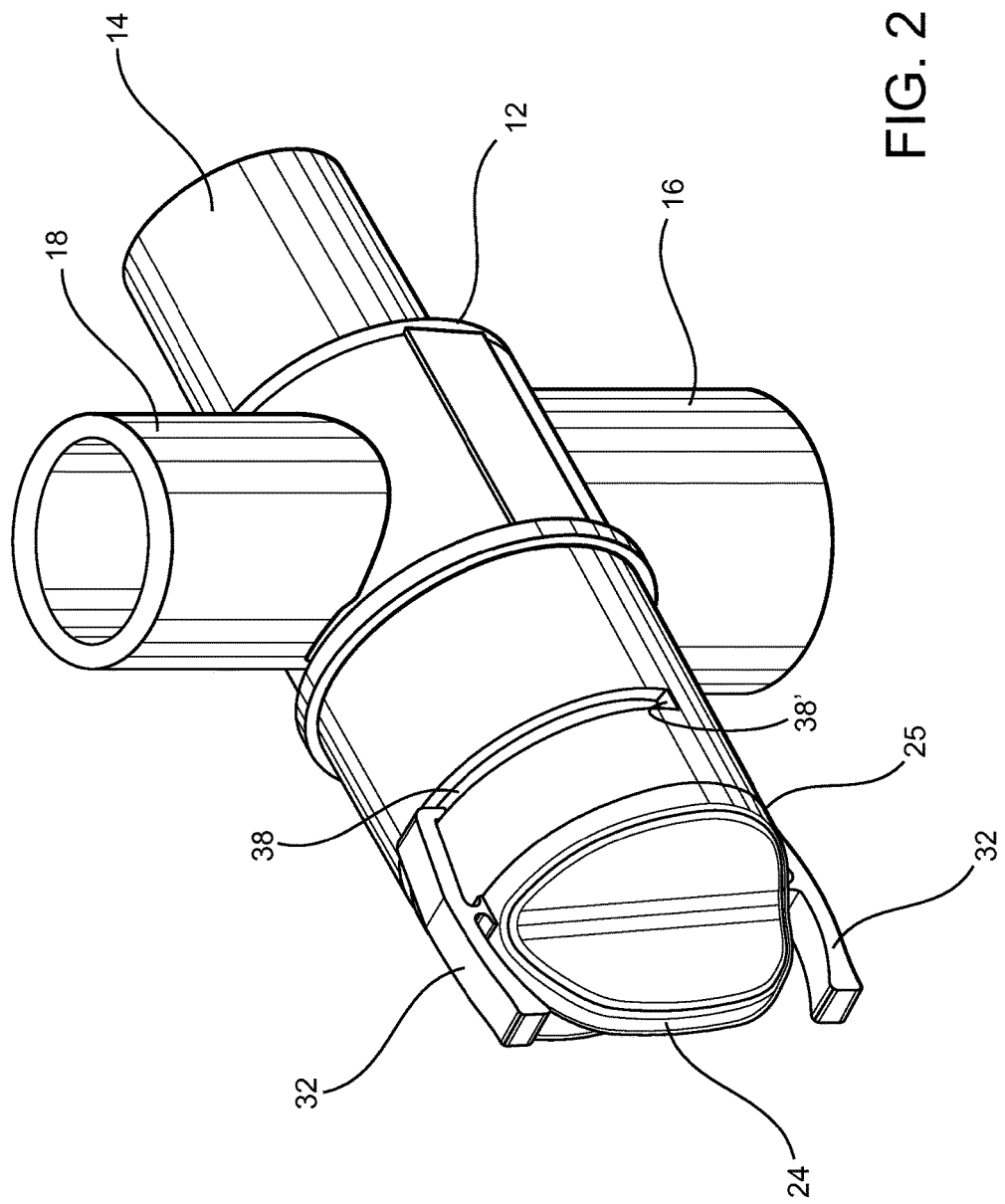
FIG. 2 is a perspective view of the embodiment of FIG. 1 in a closed position.
Figure 3:
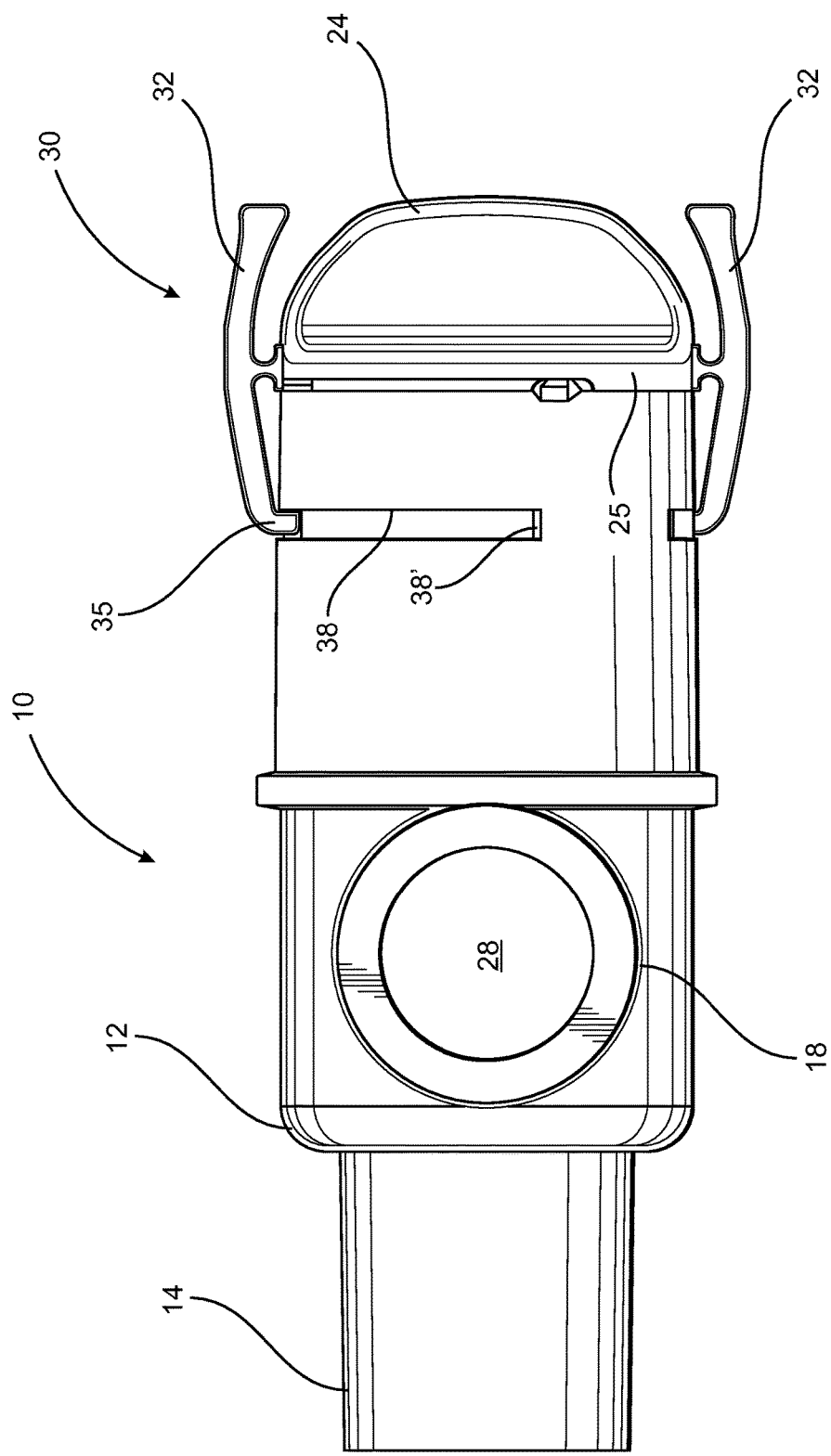
FIG. 3 is a top view of the embodiment of FIGS. 1-2 in a closed position.
Figure 4:
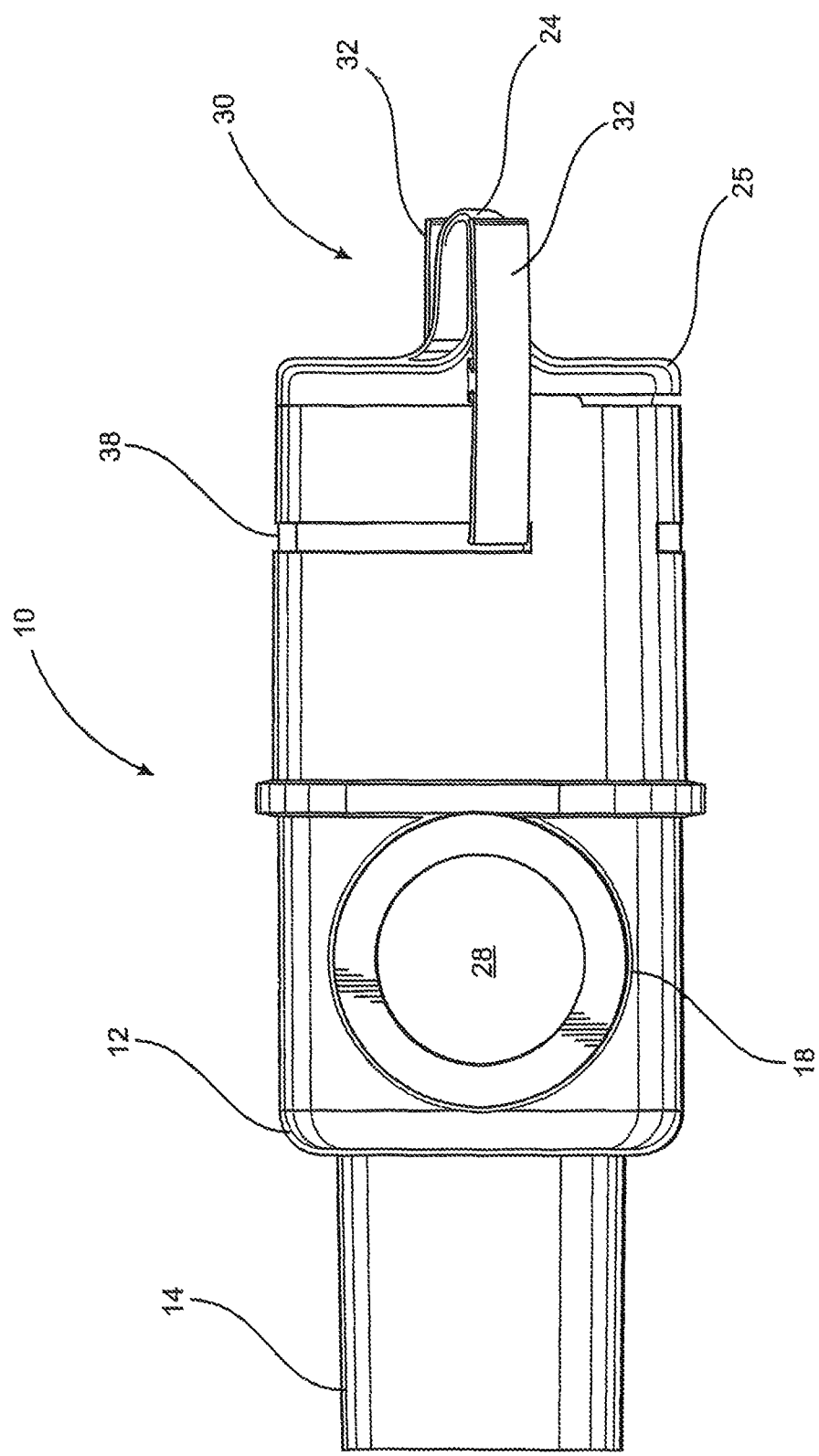
FIG. 4 is a top view of the embodiment of FIG. 3 in an open position.

With primary reference to FIGS. 1-4, the valve body 26 is selectively disposed between the aforementioned open position and closed position relative to the plurality of ports 14, 16, 18 generally, but more specifically in direct association with opening or closing of the intervention port 18. Therefore, as represented in FIGS. 1 and 3 when the valve body 26 of the valve structure 22 is rotated or otherwise appropriately disposed into the closed position, a portion of the valve body 26, such as valve stem 28 is disposed in closing and/or at least partially sealing relation to the intervention port 18. In contrast, and as represented in FIGS. 2 and 4, rotational other selective movement of the valve body 26, through manipulation of the handle or grip 24, will result in an opening of the intervention port 18. Once the intervention port 18 is opened, clear, direct communication of an applied intervention device is permitted into the hollow interior of the housing 12. The intervention device may then further proceed into the interior of the airway port 16 and extend along the length of the artificial or natural airway of the patient.

Figure 5:
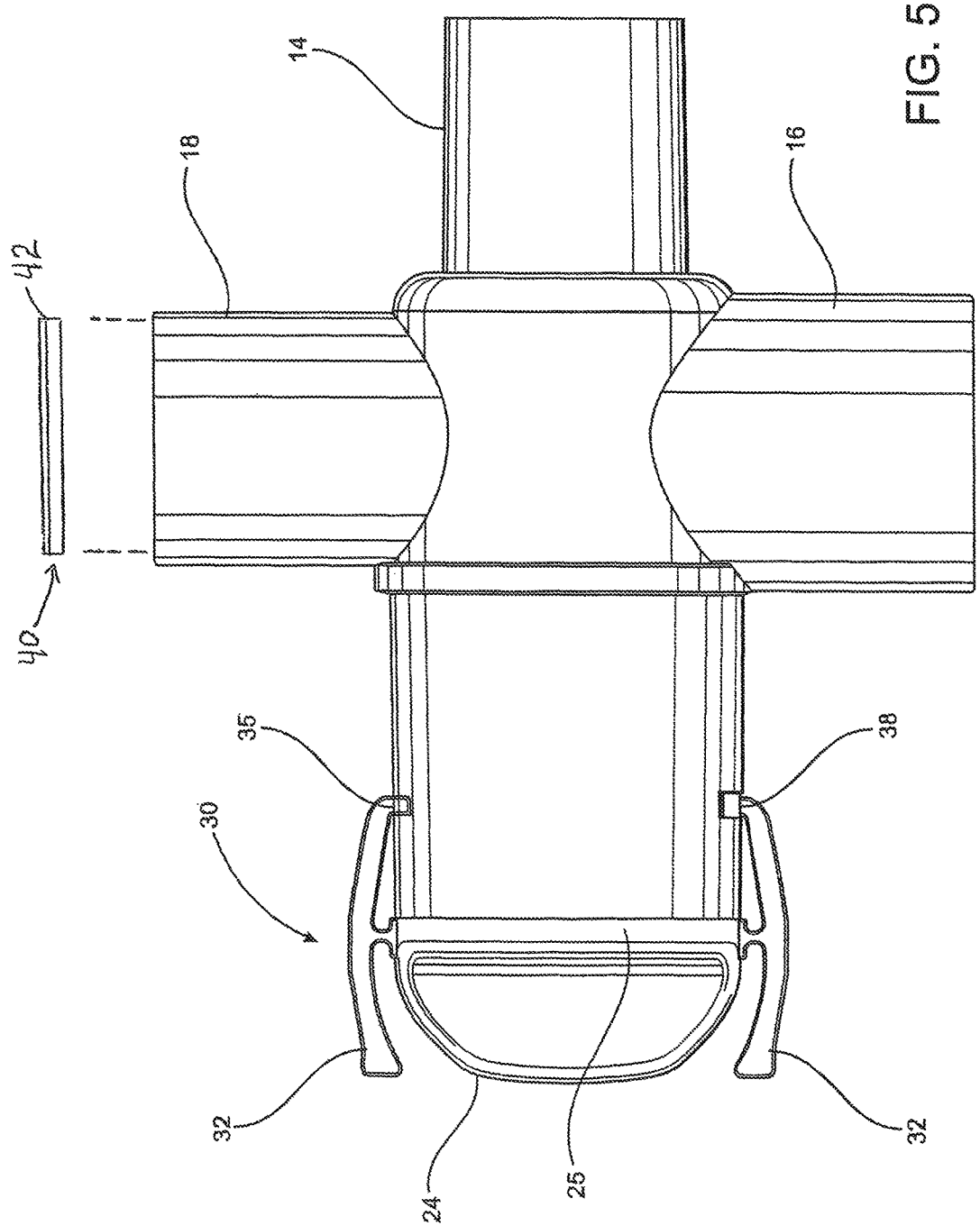
FIG. 5 is a side view of the embodiment of FIGS. 1-4 in partially exploded form.
Figure 6:
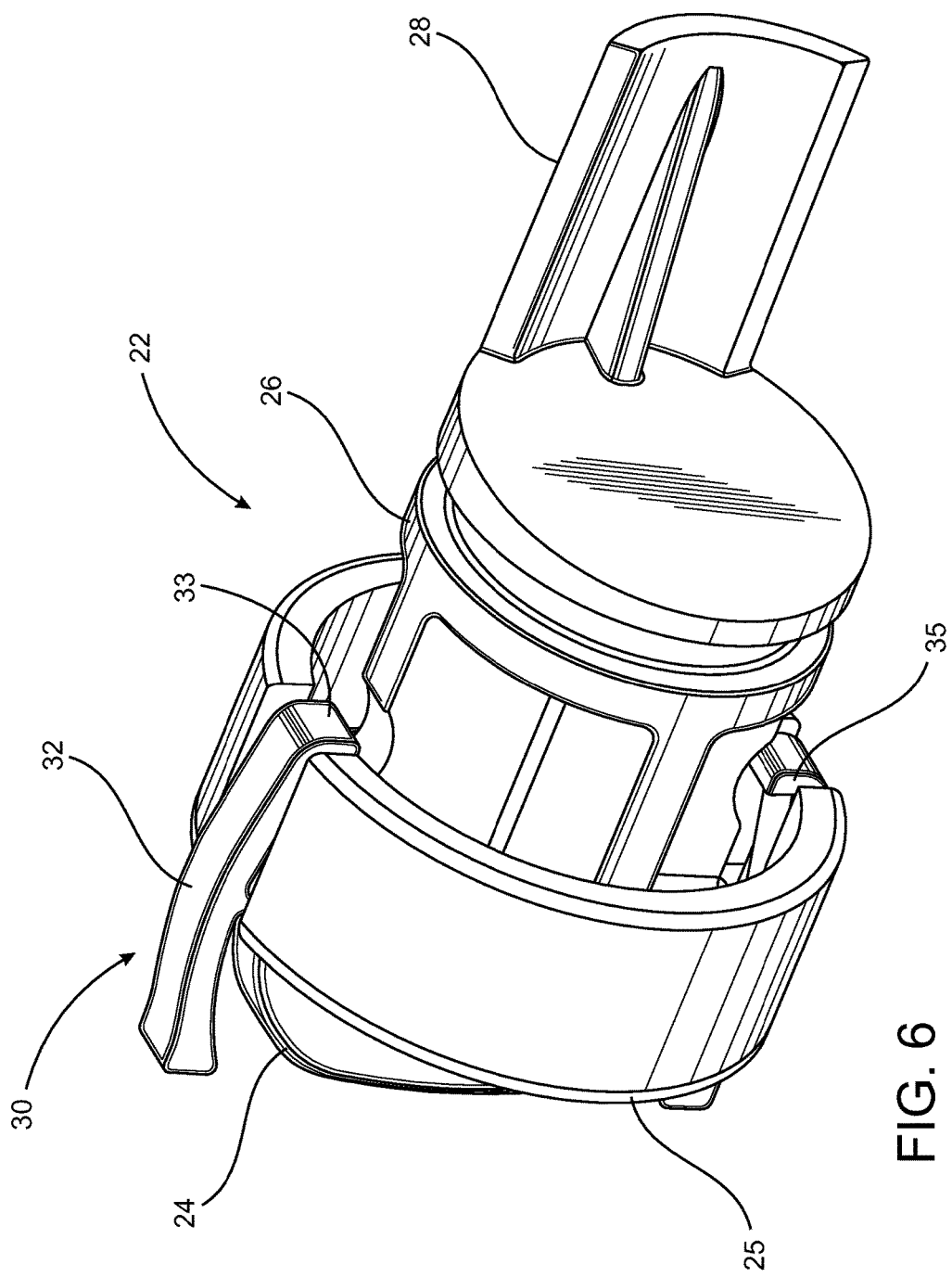
FIG. 6 is a perspective view of a valve structure represented in FIGS. 1-5 in an assembled orientation with a remainder of the connector assembly.

As represented in FIG. 6, the valve structure 22 includes the aforementioned valve body 26 and an elongated and or outwardly extending valve stem 28. The disposition of the valve body 26 in the open or closed position may thereby be more specifically defined by the disposition of the valve stem 28 in closing, sealing relation to the intervention port, as represented in FIGS. 1 and 3 or in a completely or partially open relation, out of sealing or closing relation to the intervention port 18, as represented in FIGS. 2 and 4. It is emphasized that the structural configuration of the valve body 26 may vary at least to the extent of having a different valve stem 28 or an absence of such a valve stem 28. However, in any of a possible variety of structural embodiments of the valve structure 22 and valve body 26, a portion of the valve body 26 must be cooperatively structured to assume the closed, sealing relation of the intervention port 18, as generally described above. With further regard to FIG. 6, the valve body 26 includes the aforementioned end portion 25 having the grip or handle portion 24. However, as also represented in FIGS. 1-5 the valve structure 22 also includes a retaining assembly 30 comprising at least one and/or a plurality of retaining members 32. Each of the one or more retaining members 32 is mounted on or connected to the valve structure 22 and is completely or at least partially exteriorly accessible on the housing 12. Further, the one or more retaining members 32 are disposed and structured to establish and removably maintain an interconnecting, retaining connection between the valve structure 22 and an exterior portion of the housing 12.

As set forth above, disposition of the valve structure 22 between the open and closed positions is accomplished by rotating or facilitating other appropriate movement of the valve structure when it is located within the valve port 20. However, during such movement within the valve port 20, the one or more retaining members 32 serve to maintain an attachment or connection of the valve structure 22 to the connector body 12, within the valve port 20. In order to facilitate the rotation of the valve structure 22 between the open and closed positions, the retaining assembly further includes a retaining structure formed on the exterior surface of the connector body 12. Such a retaining structure preferably includes at least one channel or groove 38 integrally formed in recessed relation to the exterior surface of the body 12. As should be noted, the number of channels 38 correspond to the number of retaining members 32 for the reasons set forth hereinafter. Moreover, each of the one or more retaining members 32 may include a flexible and/or biased structure which may be more specifically defined, in at least one embodiment, as a "living hinge".

The normal orientation of the one or more retaining members 32 includes a distal end having a retaining flange 35 formed thereon. Each of the one or more retaining flanges 35 is therefore normally biased into the interior of a correspondingly disposed one of the one or more channels 38. The configurations, dimensions and overall structural features of the retaining channels 38 and the retaining flanges 35 are such as to allow reciprocal movement of the retaining flanges 35 along the length of the corresponding channels 38 as the valve structure 22 is rotated either completely or partially between the open and closed positions. Further, the length of each of the channels 28 is such as to facilitate a clear indication of the valve structure 22 being disposed in either the closed orientation of FIGS. 1 and 3 or the open orientation of FIGS. 2 and 4, as the retaining flanges 35 engage the opposite, closed ends 38' of corresponding ones of the retaining channels 38.

Yet another structural and operative feature of one or more preferred embodiments of the present invention is at least schematically represented in FIG. 5. More specifically, a gasket structure generally indicated as 40 may include at least one gasket 42 or a set of such gaskets 42, which are individually or collectively structured to establish a sealing engagement with interventional devices (not shown) entering the intervention port 18. Further, the one or more gaskets 42 may be disposed and structured to seal a predetermined portion of the interior lumen of the intervention port 18 from the exterior and/or interior of the housing 12. The intervention port 18 may be so sealed by the gasket structure 40 independently of or in combination with an intended interventional device of a specific diameter. The inclusion of the one or more gaskets 42, in the manner described, provides a continuous preservation of airway pressure (PEEP) within the ventilator circuit, including the housing 12. This will be true despite the fact that the "closed ventilator circuit" is being accessed by anyone of a variety of interventional devices passing into and through the intervention port 18. Further, the gasket structure 40 and one or more sealing, pliable material gaskets 42 may be used independently or in cooperation with sealing and or gasket coupler structures associated with the intervention device being applied to the housing 12.

As set forth in detail hereinafter, use of the connector assembly 10 with any one of a variety of different interventional devices will be described. For purposes of clarity a representative interventional device is not disclosed in the figures. However, any one or more of a variety of conventional or customized intervention devices may be applied to the connector assembly 10, through the hollow interior of the housing 12 by entry through the intervention port 18. Further, specific representations of the ventilation tubing, airway tubing or other structural components associated with an appropriate ventilator system are also not shown for purposes of clarity, since a wide variety of such medical components or equipment may be utilized, due to the enhanced versatility of the one or more embodiments of the connector assembly 10 of the present invention.

Accordingly, at least one preferred method of use of one or more embodiments of the connector assembly 10 of the present invention comprises disposing the valve structure 22 into the aforementioned closed position. This serves to seal or prevent access of an intervention device through the intervention port 18 into the interior of the housing 10. The airway port 16 of the connector body 12 is then attached to an endotracheal tube or tracheostomy tube. Similarly a ventilator tube is connected to the ventilator port 14 thereby preliminarily establishing a ventilator circuit of bidirectional fluid flow between the ventilator supply via the ventilator tube and the artificial airway tube connected to the airway port 16. With the intervention port 18 being closed, due to rotation or other movement of the valve structure 22 into the closed position, as represented in FIGS. 1 and 3, and with the valve structure 22 operatively disposed within the interior of the valve port 20, the connector body 12 preserves therapeutically administered airway pressure (positive and expiratory pressure-PEEP) within and between the ventilator breathing circuit and the patient airway.

A selected interventional device is then connected, possibly by way of its gasket coupler, to the intervention port 18. As is recognized, each intervention device may be equipped with its own coupler and its coupler may be equipped with a sealing gasket. Such sealing gasket may be used in cooperation with the gasket structure 40, 42 as set forth above. The distal end of the interventional device is introduced through the gasket coupler and/or the gasket structure 40, 42 and into the interior lumen of the intervention port 18 on the connector body 12. Due to the fact that the intervention port 18 is closed, upon manipulation of the valve structure 22 into the closed position, a pressurized ventilator and patient breathing circuit is maintained.

The intervention port is opened by rotationally or otherwise movably disposing the valve structure 22 into a fully opened position, as represented in FIGS. 2 and 4. This disposes the interior lumen of the intervention port 18 in an unobstructed, fluid communication with the airway port 16. Concurrently, airway pressure within the patient airway and within the ventilator breathing circuit remains unchanged by the opening of the intervention port valve 18. Again, this is due to the gasket coupler and or gasket structure 40, 42 maintaining the airway circuit effectively closed during use and introduction of the interventional device. The interventional device is advanced through the housing 12 in a generally unobstructed, resistance free manner to the desired depth within the patient airway. At any point during use and disposition of the interventional device through the connector housing 12, the intervention port 18 may be disposed in a partially open and/or partially closed position through rotation or other manipulated movement of the valve structure 22, serving to position the valve body 26 in a corresponding partially open and or partially closed position. More specifically, a temporary holding or gripping force may be applied to the interventional device disposed through the intervention port 18 by positioning the valve stem 22 or other sealing portion of the valve structure 26 into an at least partially closed orientation. This results in the temporary exertion of a holding or gripping force on the interventional device. Naturally, the interventional device may be released from this temporary holding position by reversing the rotation or movement of the valve structure 22 and/or valve body 26. Accordingly, at some point during the procedure it may be beneficial to hold the inner eventual device in a fixed position by manipulating the valve body 26 in the manner set forth above. However, once the valve structure 22 is moved to a fully open position, as schematically represented in FIGS. 2 and 4, the interventional device may be freely maneuvered by the attending medical personnel in a generally resistance free manner.

Once the interventional device is withdrawn from the patient airway, it's distal end may be temporarily held or maintained within the interior lumen of the intervention port 18. This is due to the presence of a gasket coupler on the intervention device and/or the gasket structure 40, 42 associated with the intervention port 18. Once the intervention device is so disposed within the lumen of the intervention port 18, the valve body 26 is rotated to a fully closed position thereby sealing isolating the lumen of the intervention port 18 from the interior of the container body 12. Due to the fact that the interior of the intervention port 18, into which the distal tip of the intervention device is temporarily held, a desired pressure and fluid flow between the ventilator port 14 and the airway port 16, defining the ventilator breathing circuit is maintained. The tip of the intervention device may then be removed from its temporarily isolated position within the interior lumen of the intervention port 18, such as by passing through the gasket structure 40, 42.

Figure 7:
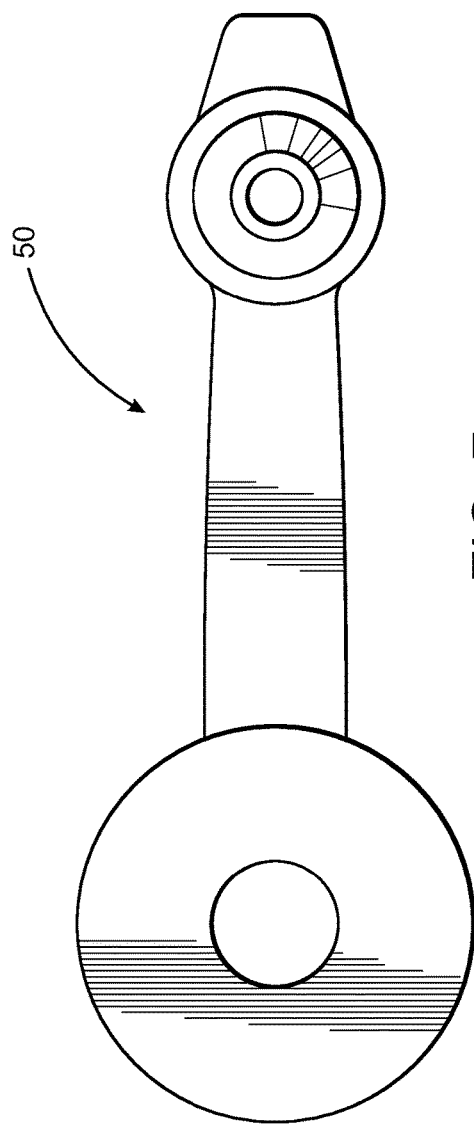
FIG. 7 is a top view of at least one accessory that may be used with the embodiment of FIGS. 1-6.
Figure 8:
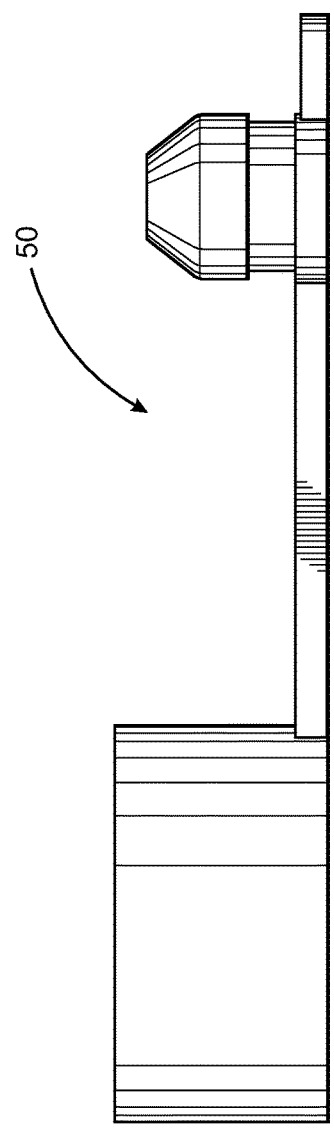
FIG. 8 is a side view of the accessory device of FIG. 7.

As represented in FIGS. 7 and 8 the intervention port 18 may be closed using an appropriate closure 50 of the type represented, but not limited thereto.

Accordingly, following the initial positioning or connection of the airway port 16 with the endotracheal tube or tracheostomy tube, as well as the ventilator breathing circuit with the ventilator port 14, the connector assembly 10 and connector housing 12 preserves therapeutically administered positive and expiratory pressure (PEEP) within and between the ventilator breathing circuit and the patient's natural airway. With the intervention port 18 in a fully closed orientation, "PEEP" is preserved by the valve body 26 sealing off communication between the interior lumen of the intervention port 18 and the interior of the connector body 12. Further, with the valve structure in a partly or fully open orientation during an intervention, "PEEP" is preserved due to the presence of the gasket structure 40, 42 secured in an appropriate position relative to the intervention port 18. As a result, uninterrupted bidirectional flow of fluid between the patient and the ventilator circuit is accomplished while "PEEP" is preserved. Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A connector assembly for a medical ventilator system, said connector assembly comprising:
   a housing comprising a plurality of ports structured to connect a ventilator in fluid communication with a patient airway,
   a valve structure movably connected to said housing and disposable into an open position and a closed position relative to at least one of said plurality of ports, and said plurality of ports including an intervention port disposed and structured to introduce an intervention device into said housing and the patient airway;

said plurality of ports further including a valve port;

said valve structure comprising a valve body movable within said valve port between said open position and said closed position;

a retaining assembly removably connecting said valve body to said housing within said valve port;

said retaining assembly comprising at least one retaining member mounted on said valve body and moveable therewith relative to and in retaining engagement with said housing; and said retaining assembly further comprising a channel formed on an exterior of said housing, said at least one retaining member movably disposed, at least partially, within said channel in retaining, interconnecting relation between said valve body and said housing.

2. The connector assembly as recited in claim 1, wherein said valve structure is removably disposed within said valve port.

3. The connector assembly as recited in claim 2, wherein said valve port is disposed in fluid communication with a remainder of said plurality of ports within a hollow interior of said housing.

4. The connector assembly as recited in claim 1, wherein said movable disposition of said valve body within said valve port between said open position and said closed position is relative to said intervention port.

5. The connector assembly as recited in claim 1, wherein said plurality of ports further comprise a ventilator port and an airway port respectively disposed and structured to connect ventilator tubing an artificial airway in fluid communication with one another via said housing.

6. The connector assembly as recited in claim 5, wherein said valve port is disposed in fluid communication with at least said airway port, upon an absence of said valve structure within said valve port, said valve port structured to connect an auxiliary device to said housing.

7. The connector assembly as recited in claim 6, wherein said closed position comprises said intervention port sealed from fluid communication with an interior of said housing and closing ventilator circuit defining fluid communication between said ventilator port and said airway port.

8. The connector assembly as recited in claim 7, wherein said open position comprises said intervention port disposed in communicating relation with said airway port concurrent to said ventilator port and said airway port being in fluid communicating relation with one another.

9. The connector assembly as recited in claim 5, wherein said closed position comprises said intervention port sealed from fluid communication within said housing and a closed ventilator circuit defining fluid communication between said ventilator port and said airway port.

10. The connector assembly as recited in 5, wherein said open position comprises said intervention port disposed in communicating relation with said airway port concurrent to a fluid communicating relation between said ventilator port and said airway port.

11. The connector assembly of claim 1, wherein said at least one retaining member comprising a living hinge disposable into biased, retaining engagement with an exterior of said housing.

12. The connector assembly of claim 1, wherein said valve body comprises an end portion exteriorly accessible on said housing, said end portion structured for manual disposition of said valve structure between said open position and said closed position.

13. The connector assembly as recited in claim 12, wherein said end portion is disposed and structured for rotation of said valve body within said valve port, between said open position and said closed position, relative to said intervention port.

* * * * *